(12) United States Patent
Helm

(10) Patent No.: US 9,180,275 B2
(45) Date of Patent: Nov. 10, 2015

(54) CATHETER-DRESSING SYSTEMS WITH INTEGRATED FLUSHING MECHANISMS

(76) Inventor: Robert E. Helm, Rye Beach, NH (US)

(*) Notice: Subject to any disclaimer, the term of this patent is extended or adjusted under 35 U.S.C. 154(b) by 15 days.

(21) Appl. No.: 13/613,509

(22) Filed: Sep. 13, 2012

(65) Prior Publication Data

US 2013/0178825 A1 Jul. 11, 2013

Related U.S. Application Data

(63) Continuation-in-part of application No. 13/349,909, filed on Jan. 13, 2012, now Pat. No. 8,715,242.

(60) Provisional application No. 61/534,981, filed on Sep. 15, 2011, provisional application No. 61/437,862, filed on Jan. 31, 2011, provisional application No. 61/482,124, filed on May 3, 2011, provisional application No. 61/482,564, filed on May 4, 2011.

(51) Int. Cl.
*A61M 25/02* (2006.01)
*A61M 39/18* (2006.01)
*A61M 25/06* (2006.01)

(52) U.S. Cl.
CPC ............ *A61M 25/0606* (2013.01); *A61M 25/02* (2013.01); *A61M 25/0631* (2013.01); *A61M 39/18* (2013.01); *A61M 2025/028* (2013.01); *A61M 2025/0253* (2013.01)

(58) Field of Classification Search
CPC ............... A61M 2025/0253; A61M 2025/026; A61M 2025/028; A61M 25/06; A61M 25/0606; A61M 25/02; A61M 25/0631; A61M 39/18

USPC ............... 604/506, 264, 272, 164.02, 164.05, 604/164.08, 164.04, 103.01
See application file for complete search history.

(56) References Cited

U.S. PATENT DOCUMENTS 2,461,891 A * 2/1949 Giles ............................ 222/101
3,198,385 A * 8/1965 Maxwell ....................... 604/131
3,683,911 A 8/1972 McCormick
(Continued)

FOREIGN PATENT DOCUMENTS

DE 3140192 A1 4/1983
WO 94/05239 A1 3/1994
(Continued)

OTHER PUBLICATIONS

[No Author Listed] Alibaba.com Product Literature—IV Catheter Dressing (accessed Nov. 17, 2010).
(Continued)

*Primary Examiner* — Quynh-Nhu H Vu
(74) *Attorney, Agent, or Firm* — Thomas Engellenner; Reza Mollaaghababa; Pepper Hamilton LLP

(57) ABSTRACT

Methods and devices are disclosed herein that generally involve a sterile catheter-dressing system that allows for integrated injection of fluids, e.g., a saline flush, during the process of catheter insertion and sterile dressing placement. Such methods and devices can be used as a fully integrated catheter insertion system, or to convert existing catheter insertion devices and methods into integrated flush and sterile sealing catheter-dressing systems. Such methods and devices can greatly simplify the catheter insertion process, and can allow the reproducible placement of a fully sterile and flushed vascular catheter, as well as the placement of a durably sterile circumferentially sealing and securing dressing.

24 Claims, 7 Drawing Sheets

SIDE VIEW: NEEDLE DEPLOYED, SALINE IN CHAMBER

SIDE VIEW: NEEDLE RETRACTED, SALINE FLUSHED

(56) References Cited

U.S. PATENT DOCUMENTS

| | | | |
|---|---|---|---|
| 3,918,446 A | | 11/1975 | Buttaravoli |
| 4,016,879 A | * | 4/1977 | Mellor .............................. 604/27 |
| 4,327,723 A | | 5/1982 | Frankhouser |
| 4,392,853 A | * | 7/1983 | Muto .............................. 604/171 |
| 4,464,178 A | | 8/1984 | Dalton |
| 4,515,592 A | | 5/1985 | Frankhouser |
| 4,551,136 A | | 11/1985 | Mandl |
| 4,551,137 A | | 11/1985 | Osborne |
| 4,563,177 A | | 1/1986 | Kamen |
| 4,634,433 A | | 1/1987 | Osborne |
| 4,767,411 A | | 8/1988 | Edmunds |
| 4,781,695 A | | 11/1988 | Dalton |
| 4,966,590 A | | 10/1990 | Kalt |
| 5,007,901 A | * | 4/1991 | Shields ......................... 604/110 |
| 5,074,847 A | * | 12/1991 | Greenwell et al. ............. 604/174 |
| 5,112,313 A | * | 5/1992 | Sallee .......................... 604/180 |
| 5,116,324 A | | 5/1992 | Brierley et al. |
| 5,215,532 A | | 6/1993 | Atkinson |
| 5,232,453 A | | 8/1993 | Plass et al. |
| 5,238,010 A | | 8/1993 | Grabenkort et al. |
| 5,336,195 A | | 8/1994 | Daneshvar |
| 5,344,415 A | | 9/1994 | DeBusk et al. |
| 5,372,589 A | | 12/1994 | Davis |
| 5,380,294 A | | 1/1995 | Persson |
| 5,415,642 A | | 5/1995 | Shepherd |
| D359,120 S | | 6/1995 | Sallee et al. |
| 5,478,326 A | | 12/1995 | Shiu |
| 5,577,516 A | | 11/1996 | Schaeffer |
| 5,685,865 A | | 11/1997 | Cosgrove et al. |
| 5,686,096 A | | 11/1997 | Khan et al. |
| 5,690,612 A | | 11/1997 | Lopez et al. |
| 5,694,686 A | | 12/1997 | Lopez |
| 5,702,371 A | | 12/1997 | Bierman |
| 5,707,348 A | | 1/1998 | Krogh |
| 5,715,815 A | | 2/1998 | Lorenzen et al. |
| 5,722,959 A | | 3/1998 | Bierman |
| 5,769,807 A | | 6/1998 | Haddock et al. |
| 5,772,636 A | | 6/1998 | Brimhall et al. |
| 5,776,106 A | | 7/1998 | Matyas |
| 5,807,341 A | | 9/1998 | Heim |
| 5,989,220 A | | 11/1999 | Shaw et al. |
| 6,080,138 A | | 6/2000 | Lemke et al. |
| 6,099,509 A | | 8/2000 | Brown, Jr. et al. |
| 6,132,399 A | | 10/2000 | Shultz |
| 6,302,867 B1 | | 10/2001 | Brown, Jr. et al. |
| 6,375,639 B1 | | 4/2002 | Duplessie et al. |
| 6,413,240 B1 | | 7/2002 | Bierman et al. |
| 6,569,121 B1 | | 5/2003 | Purow et al. |
| 6,571,395 B1 | | 6/2003 | Korkor |
| 6,809,230 B2 | | 10/2004 | Hancock et al. |
| 6,827,707 B2 | | 12/2004 | Wright |
| 7,083,598 B2 | | 8/2006 | Liska |
| 7,153,291 B2 | | 12/2006 | Bierman |
| 7,244,245 B2 | | 7/2007 | Purow et al. |
| 7,247,150 B2 | | 7/2007 | Bierman |
| 7,544,186 B2 | | 6/2009 | Davis et al. |
| 7,578,804 B2 | | 8/2009 | Bierman |
| 7,723,561 B2 | | 5/2010 | Propp |
| 7,744,572 B2 | | 6/2010 | Bierman |
| 7,799,001 B2 | | 9/2010 | Bierman |
| 7,806,873 B2 | | 10/2010 | Dikeman et al. |
| 8,414,543 B2 | * | 4/2013 | McGuckin et al. ........... 604/247 |
| 2002/0082559 A1 | | 6/2002 | Chang et al. |
| 2002/0092529 A1 | | 7/2002 | Rozier et al. |
| 2003/0078540 A1 | | 4/2003 | Saulenas et al. |
| 2004/0044310 A1 | * | 3/2004 | Suzuki .......................... 604/110 |
| 2005/0065479 A1 | | 3/2005 | Schiller et al. |
| 2005/0113798 A1 | | 5/2005 | Slater et al. |
| 2005/0119619 A1 | * | 6/2005 | Haining .................. 604/164.01 |
| 2005/0165355 A1 | * | 7/2005 | Fitzgerald ............... 604/164.08 |
| 2005/0261623 A1 | | 11/2005 | Propp |
| 2006/0030820 A1 | | 2/2006 | Alheidt et al. |
| 2006/0211994 A1 | | 9/2006 | Roman et al. |
| 2006/0247577 A1 | | 11/2006 | Wright |
| 2006/0247582 A1 | | 11/2006 | Alheidt et al. |
| 2006/0264836 A1 | | 11/2006 | Bierman |
| 2007/0027429 A1 | | 2/2007 | Kuracina et al. |
| 2007/0055205 A1 | * | 3/2007 | Wright et al. ................. 604/174 |
| 2007/0060892 A1 | | 3/2007 | Propp |
| 2008/0058692 A1 | | 3/2008 | Propp et al. |
| 2008/0125750 A1 | | 5/2008 | Gaissert |
| 2008/0221531 A1 | | 9/2008 | Alheidt et al. |
| 2008/0262439 A1 | | 10/2008 | Alheidt |
| 2008/0300574 A1 | * | 12/2008 | Belson et al. ................. 604/510 |
| 2009/0118696 A1 | | 5/2009 | Nyhart, Jr. |
| 2009/0192470 A1 | | 7/2009 | Propp |
| 2009/0306602 A1 | | 12/2009 | Elwell et al. |
| 2009/0318891 A1 | * | 12/2009 | Marcotte et al. .............. 604/510 |
| 2010/0100049 A1 | | 4/2010 | Godfrey |
| 2010/0179482 A1 | | 7/2010 | Wright et al. |
| 2010/0249706 A1 | * | 9/2010 | Clemente ...................... 604/154 |
| 2011/0106014 A1 | | 5/2011 | Helm, Jr. |
| 2012/0197204 A1 | | 8/2012 | Helm, Jr. |
| 2012/0232489 A1 | | 9/2012 | Helm, Jr. |

FOREIGN PATENT DOCUMENTS

| | | |
|---|---|---|
| WO | 9702848 A1 | 1/1997 |
| WO | 2008117078 A1 | 10/2008 |

OTHER PUBLICATIONS

[No Author Listed] Become.com Product Literature—3m Catheter Dressing (accessed Nov. 17, 2010).

[No Author Listed] IV Team, BD Announces UK Launch of new BD Nexiva(TM) Closed IV Catheter System Designed to Help Protect Healthcare Workers, PR Newswire.com, Jul. 29, 2009.

[No Author Listed] Seattle Treatment Education Project, The Body, The Facts About Intravenous Catheter Lines, thebody.com, Oct. 1992.

[No Author Listed] "Silverlone® Lifesaver198 Ag" 7 Day Antimicrobial IV/Catheter Dressing Product Literature, silverlon.com (accessed Nov. 17, 2010).

[No Author Listed] Smith & Nephew Product Literature—I.V. and Catheter Sites, smith-nephew.com (accessed Nov. 17, 2010).

[No Author Listed] Sorbaview Shield Product Literature, centurionmp.com (accessed Nov. 17, 2010).

[No Author Listed] Walgreens.com Product Literature—Medline Suresite I.V. Transparent Catheter Dressing 2×3 (accessed Nov. 17, 2010).

Australian Office Action issued Jun. 20, 2012 for Application No. 2010319924 (5 Pages).

Clemens, Mary, New IV Dressing Benefits Both the Patient and Clinician, Reuters.com, Feb. 2, 2009.

International Search Report and Written Opinion mailed Jul. 20, 2011 for Application No. PCT/US10/054427.

International Preliminary Report on Patentability for Application No. PCT/US2010/054427 mailed May 10, 2012 (7 Pages).

International Search Report and Written Opinion mailed Aug. 17, 2012 for Application No. PCT/US2012/021196 (12 Pages).

Johnson, Maree, M.D., Systematic Review Central Line Dressing Type and Frequency, Joanna Briggs Institute, Jan. 20, 1998.

Maki DG, and Ringer M., Evaluation of dressing regimens for prevention of infection with peripheral intravenous catheters. Gauze, a transparent polyurethane dressing, and an iodophor-transparent dressing., JAMA. Nov. 6, 1987;258 (17):2396-403., pubmed.gov.

McGee, David C, M.D. and Michael K. Gould, M.D., Preventing Complications of Central Venous Catheterization, N. Engl J Med 2003; 348:1123-1133.

Australian Office Action issued Nov. 1, 2012 for Application No. 2010319924 (3 Pages).

Supplemental European Search Report mailed Apr. 18, 2013 for Application No. 10830440.3 (7 Pages).

International Preliminary Report on Patentability and Written Opinion of the International Searching Authority of PCT/US2012/055066, mailed Mar. 27, 2014 (7 pages).

* cited by examiner

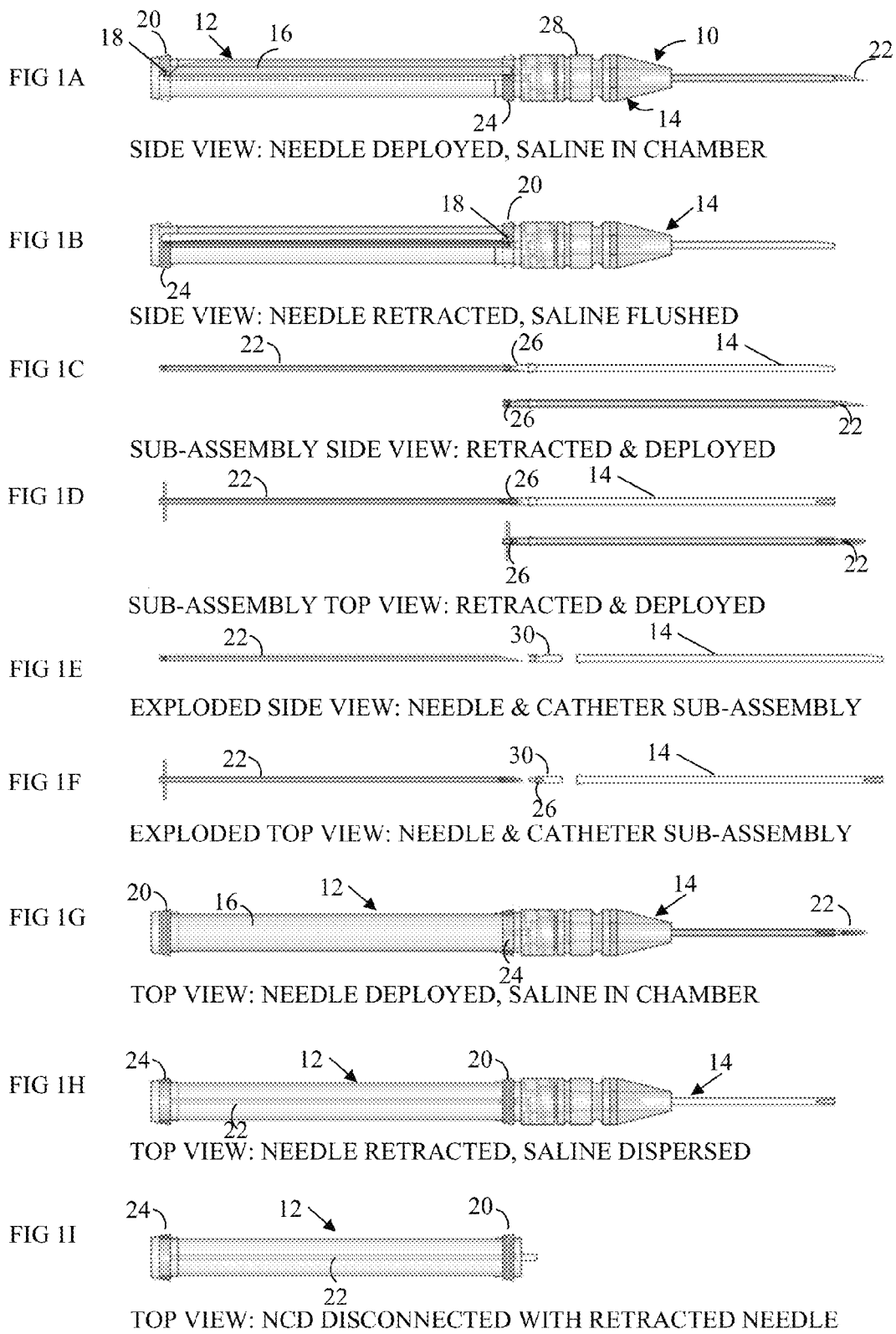

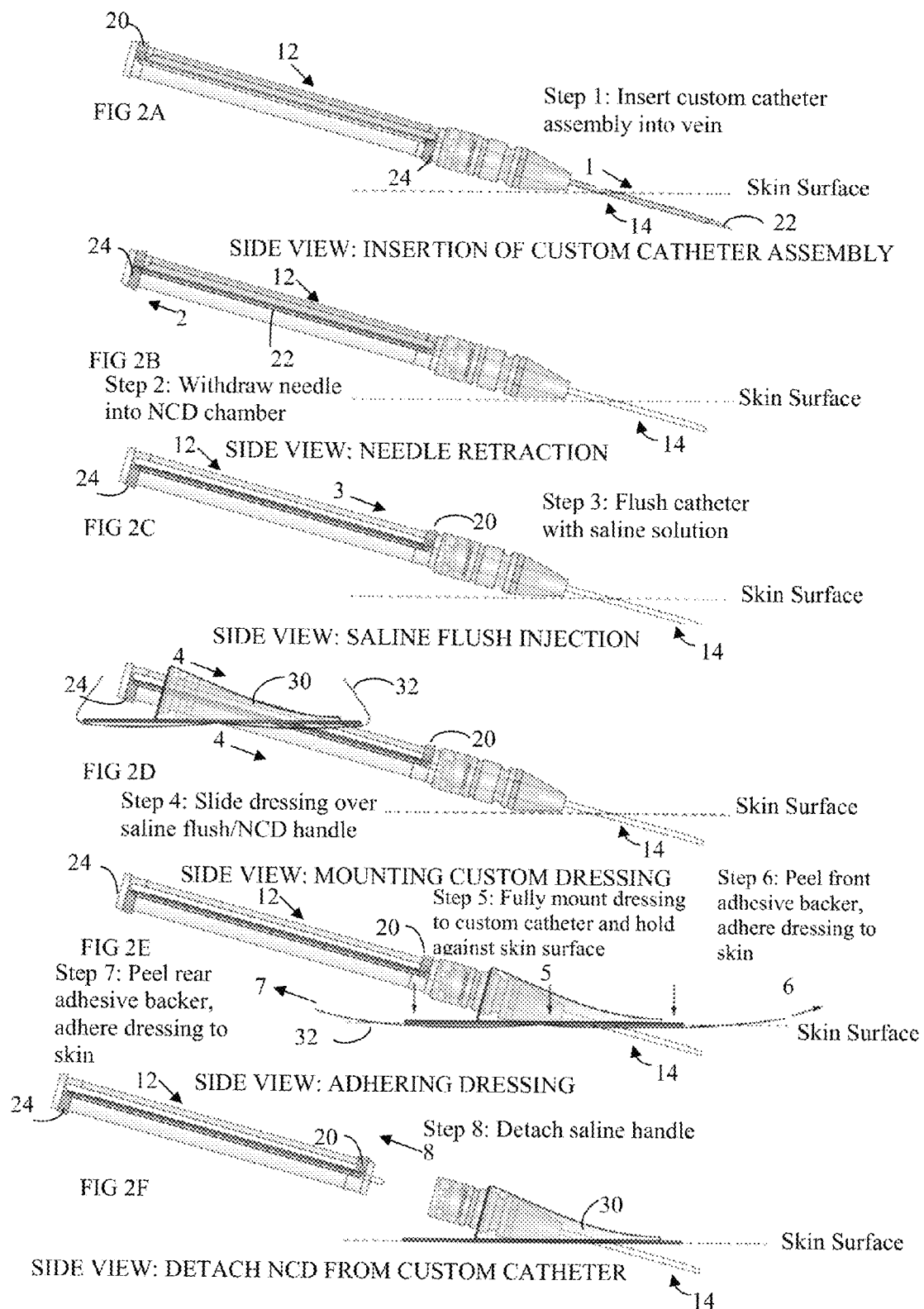

SIDE VIEW: SALINE IN CHAMBER, CONNECTED TO LUER LOCK

SIDE VIEW: SALINE INJECTED, CONNECTED TO LUER LOCK

SIDE VIEW: SALINE INJECTED, DISCONNECTED FROM LUER LOCK

SIDE VIEW: SALINE IN CHAMBER, CONNECTED TO CLAVE® CONNECTOR

SIDE VIEW: SALINE INJECTED, CONNECTED TO CLAVE® CONNECTOR

SIDE VIEW: SALINE INJECTED, DISCONNECTED FROM CLAVE® CONNECTOR

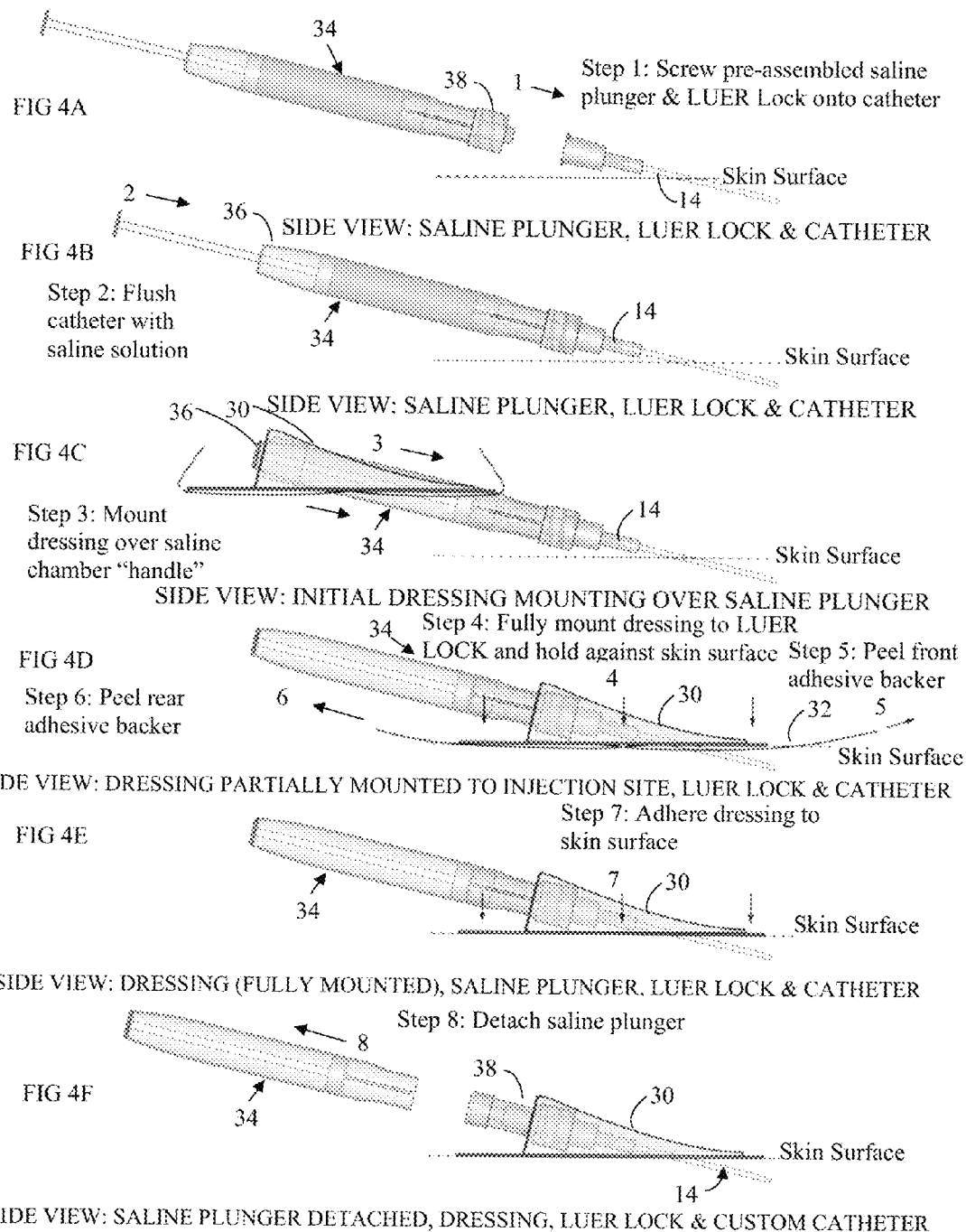

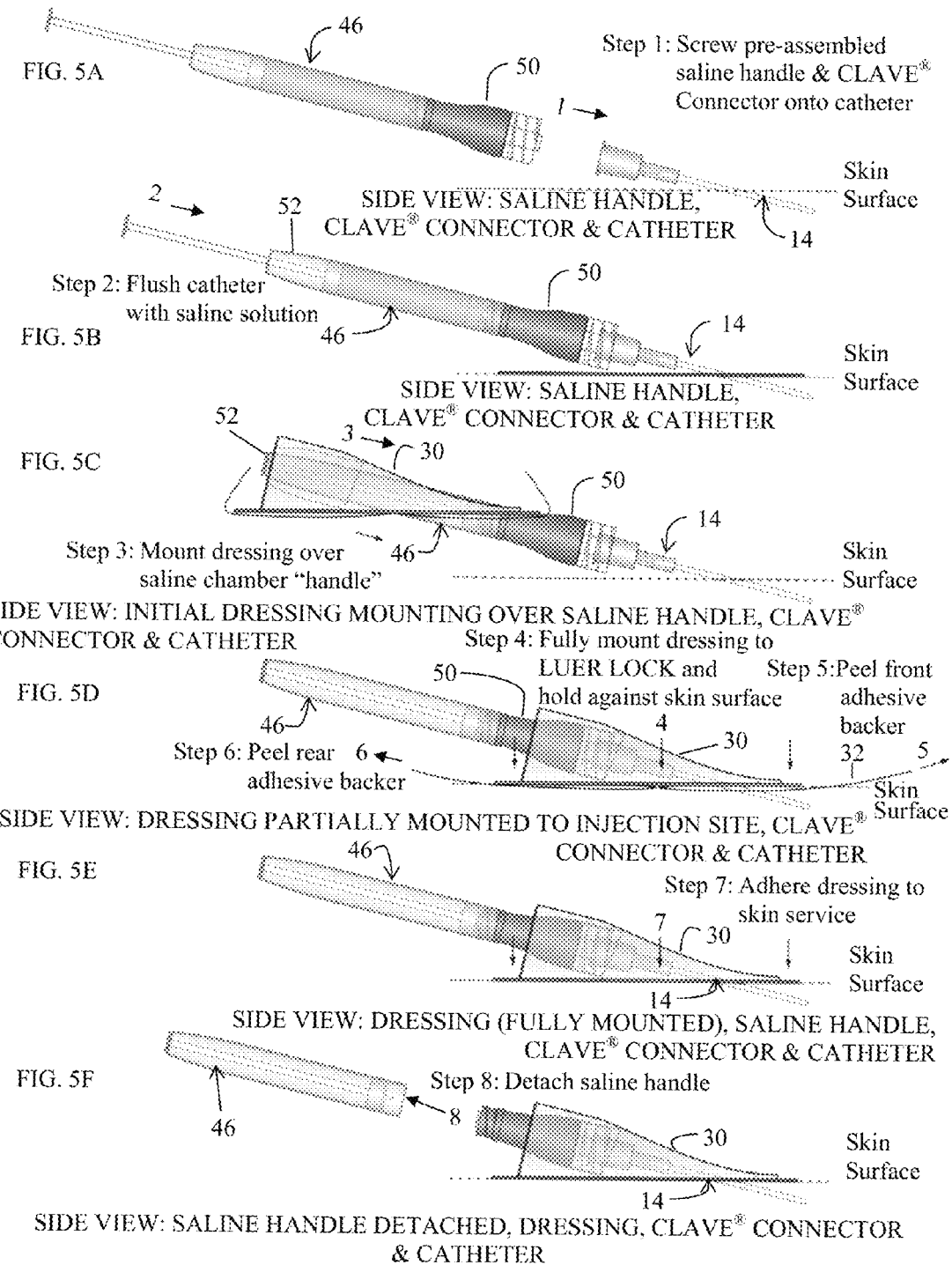

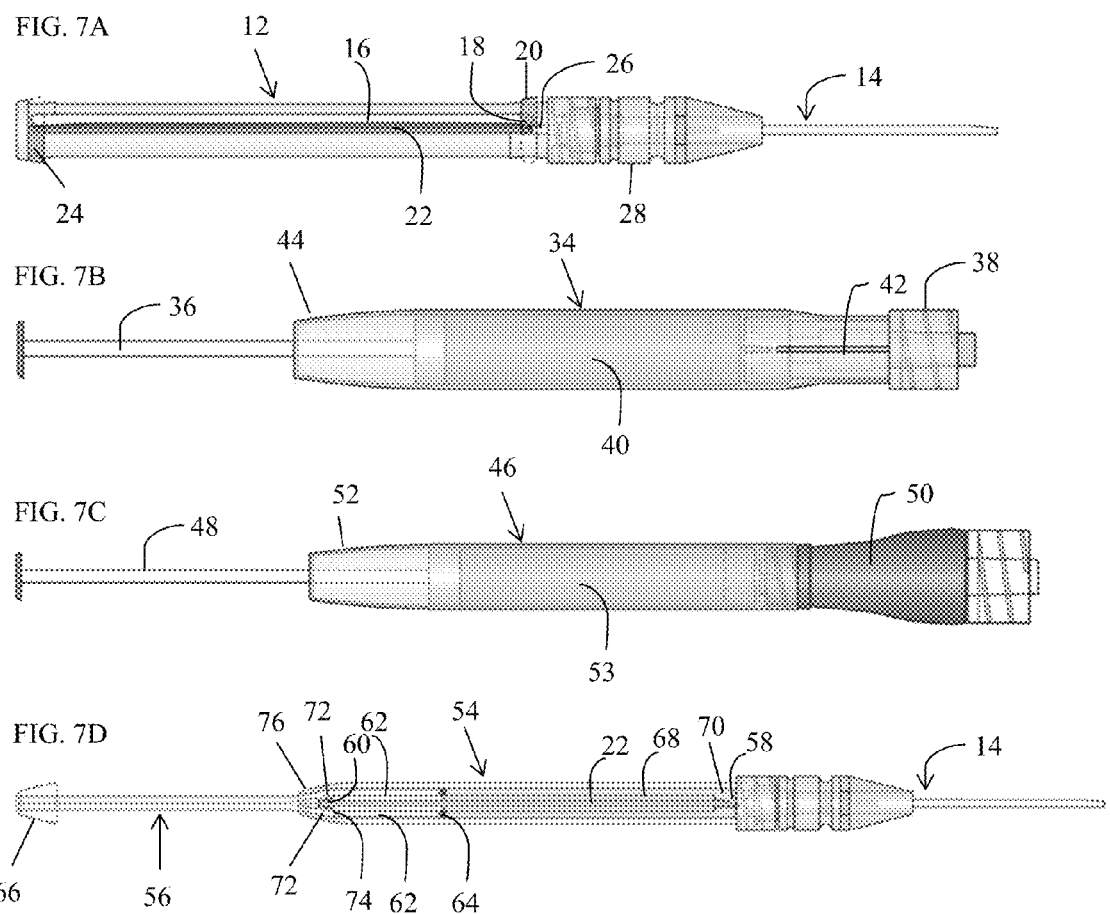

CATHETER-DRESSING SYSTEMS WITH INTEGRATED FLUSHING MECHANISMS

CROSS-REFERENCE TO RELATED APPLICATIONS

This application claims priority to U.S. Provisional Application No. 61/534,981, filed on Sep. 15, 2011, which is hereby incorporated by reference in its entirety. This application is also a continuation-in-part of, and claims priority to, U.S. patent application Ser. No. 13/349,909, filed Jan. 13, 2012 (now U.S. Pat. No. 8,715,242, issued May 6, 2014), which in turn claims the benefit of priority of U.S. Provisional Patent Application No. 61/437,862, filed on Jan. 31, 2011, U.S. Provisional Patent Application No. 61/482,124, filed May 3, 2011, and U.S. Provisional Patent Application No. 61/482,564, filed May 4, 2011.

FIELD

The present invention relates to catheter-dressing systems with integrated flushing mechanisms and related methods.

BACKGROUND

During placement of an intravascular catheter, the current standard of care technique includes flushing of the newly inserted catheter with sterile saline solution to clear the hub and catheter of blood that would otherwise coagulate and result in loss of catheter function. Present standard catheter placement and flush methodology involves several separate, often one-handed, sequential steps using non-sterile gloves.

First, the insertion site is prepped with sterilizing solution (e.g., chlorhexidine). Second, using non-sterile gloves, the vascular catheter is inserted through the skin and into the blood vessel, taking care not to touch the actual insertion site or catheter with the non-sterile gloves. Third, with one hand, the insertion needle is withdrawn from the catheter and put aside (e.g., on a bed or side table). During this time, the other hand stabilizes the catheter hub and applies pressure to the blood vessel upstream from the insertion site to prevent backbleeding. Care must be taken not to touch the insertion site (either the catheter or the surrounding skin) with the non-sterile gloved hand. Fourth, the hand that withdrew the needle then reaches for and obtains from the local area (e.g., bed or side table) an IV hub cap device (e.g., a Luer Lock® connector, a Clave® connector, or extension tubing with attached Clave®), which is placed both to prevent backflow of blood into the catheter and to allow for mechanical connection to, and use of, the catheter. The hub cap device packaging has been pre-opened and set aside within reach to allow one-handed pick up and manipulation of the hub cap during this process.

Fifth, the free hand then reaches for and obtains from the local area (e.g., bed or side table) a syringe that has been pre-filled with sterile saline. Sixth, the syringe is attached to the hub cap device, and the saline solution is injected/flushed into the connection device-catheter complex to displace blood from the catheter into the blood vessel, leaving the catheter filled with saline solution. Seventh, the syringe is detached and put aside. Eighth, and finally, a "sterile" dressing is then placed over the catheter hub and skin insertion site (although often at this point neither the catheter or dressing is sterile, as during the process they have been touched repeatedly by non-sterile gloved fingers). Additional adhesive tape is then applied to further secure and position the catheter.

Wide variations in this process occur, leading consequently to highly-variable results. One common variation is to flush the catheter with saline prior to placing the hub cap device. In other instances, an IV line is attached directly to the hub and IV fluid administration initiated (thereby negating the need for saline flush). In all instances, the technique is awkward, requires the use of multiple complex one-handed maneuvers at multiple time points, and requires use of an often unprepared working area beyond the actual insertion site (e.g., bed or side table)—an area that is usually not sterile/clean.

Looming over this standard vascular catheter insertion process is the desire for sterility and the prevention of outside organisms (e.g., hospital environment bacteria) from reaching the catheter insertion site. While this is the goal, in reality it is extremely difficult to achieve. The complexity of the catheter insertion and flush procedure, combined with the fact that it is done over such a broad and varied working area with non-sterile gloves, leaves multiple points for loss of sterile technique. All too often, the end result of this highly complex and variable process is a non-sterile catheter and catheter insertion site. This lack of sterility is compounded over time by the placement of a non-sealing dressing that cannot maintain sterility even if it is able to be achieved initially. The result is the increased loss of catheters from site infection, and the need to change catheters and dressings at relatively frequent intervals in hopes of preventing clinical expression of catheter infection. One very clear marker of the inadequacy of existing catheter insertion-dressing placement technique is the increasing reliance on compensatory measures such as antimicrobial adjuncts and supplementary securement devices.

Accordingly, a need exists for improved methods and devices for sterile placement and maintenance of catheters.

SUMMARY

Methods and devices are disclosed herein that generally involve a sterile catheter-dressing system that allows for integrated injection of a fluid, e.g., a saline flush, during the process of catheter insertion and sterile dressing placement. Such methods and devices greatly simplify the catheter insertion process, and allow the reproducible placement of a fully sterile and flushed vascular catheter, as well as the placement of a durably sterile circumferentially sealing and securing dressing.

With such methods and devices, the sterile saline catheter flush process can be simply and efficiently integrated with the processes of catheter placement and catheter dressing placement. In one embodiment, a device is provided that utilizes a needle containment device already attached to the catheter hub during catheter insertion not only as a handle for mounting and placement of a sterile dressing, but also to contain and inject sterile saline into the inserted catheter. In some embodiments, by incorporating the saline flush capability into the needle containment device, the needle containment device's "natural" pre-attached position relative to the catheter can be taken advantage of, allowing marked simplification of the saline flush process. Multiple awkward one-handed maneuvers are avoided, thereby eliminating multiple potential sterility breakpoints. Effort is fully and simply concentrated on the catheter and its pre-attached needle containment device, without the need for reaching for/utilizing non-sterile side work areas. Using these methods and devices, the use of sterile gloves becomes possible, and can be easily made routine, representing a true paradigm shift in vascular catheter placement and care.

The integrated system can also include a circumferentially sealing dressing configured to mount over the needle containment device which contains the saline flush, and into final mating/sealing position on the catheter hub.

Methods and devices are also disclosed herein which allow integrated sterile flushing of existing catheters and connection device technology (e.g., a Luer Lock® connector, or a Clave® connector) as well as simple and sterile placement of a circumferential sealing dressing. For example, in one embodiment, saline-containing tubular bodies of specified relative diameter are provided which can be pre-attached to hub cap devices (e.g., Luer Lock® connector, Clave® connector). These hub cap devices can be coupled to existing standard catheters, allowing the tubular body to be used as a "handle" to allow easy and sterile control when mounting the hub cap device to the inserted catheter hub and when subsequently attaching a sterile circumferentially-sealing dressing. In other words, the sterile flush handle can serve a dual purpose as a mounting device, whereby the circumferentially sealing dressing is slid over the handle and mounted into position on the hub cap device. Once the tubular body is attached to the catheter, injection of the saline through the attached hub cap device and through the inserted catheter to clear any contained blood then naturally follows in simple sterile fashion, without the need for reaching for and attaching a separate saline flush syringe. In some embodiments, the sterile sealing dressing can also be integrated with the hub cap device, in which case the dressing can simply be "unfurled" after the saline flush is complete. The dressing can then be adhered to the skin around the catheter insertion site. Detachment of the saline filled mounting tube completes the process.

Incorporation of the saline flush into the needle containment device, or into a saline body attached to a hub cap device, leads to a significant improvement and simplification of the catheter insertion, catheter flushing, and dressing placement processes. It allows concentration of effort at a single point, and allows these processes to be performed in a more sterile fashion. In addition, a durable and fully-sterile circumferentially sealing dressing can be placed in conjunction with existing vascular catheter technology. In some embodiments, the needle containment device preferably has a diameter that is equal to or less than that of the catheter hub, thereby allowing a sterile sealing dressing to be slid down over the needle containment device and mounted to the catheter hub in sealing engagement.

In one aspect, a catheter system is provided that includes a catheter assembly comprising an implantable catheter and catheter hub formed at a proximal end of the implantable catheter. The system also includes a needle containment device extending proximally from the catheter assembly, the needle containment device being coupled to an insertion needle disposed through an inner lumen of the implantable catheter. The needle containment device includes a chamber filled with an injectable agent and is configured to selectively place the chamber in fluid communication with the inner lumen of the implantable catheter.

The system can also include a dressing assembly configured to slide over the needle containment device and catheter hub to form a circumferential seal around the catheter hub and a catheter insertion site. The injectable agent can include sterile saline or other solution suitable for flushing a catheter. The chamber can include a flexible bag. The needle containment device can include a first hemi-cylindrical collar disposed about an exterior surface of a body portion of the needle containment device, the collar being coupled to a roller configured to compress the chamber. Sliding the first collar distally relative to the body portion can cause the roller to compress the chamber and force the injectable agent into the inner lumen of the implantable catheter. The needle containment device can include a second hemi-cylindrical collar disposed about an external surface of a body portion of the needle containment device, the collar being coupled to the insertion needle. Sliding the second collar proximally relative to the body portion can be effective to withdraw the insertion needle from the implantable catheter and into the needle containment device.

The needle containment device can include a valve that controls fluid communication between the chamber and the inner lumen of the implantable catheter. The insertion needle can block an aperture of the valve when the insertion needle is in a deployed configuration. The aperture of the valve can be open when the insertion needle is in a retracted configuration. The needle containment device can have a maximum outer diameter that is less than or equal to a diameter of a mating point on the catheter assembly to which a dressing can be mated. A circumferentially-sealing catheter dressing is adapted to be slid over the needle containment device.

The needle containment device can be divided into two or more separate compartments, at least one compartment being filled with the injectable agent. The needle containment device can include a sliding collar whose movement distally towards the catheter assembly effects pressure based transfer of the injectable agent from the chamber into the catheter assembly. The needle containment device can include a central plunger, proximal withdrawal of the plunger out of the needle containment device can serve to remove the insertion needle from the implantable catheter and lock it into a retracted position, and subsequent distal movement of the plunger can serve to effect transfer of the injectable agent from the chamber to the catheter assembly.

In another aspect, a catheter flushing device is provided that includes an elongate body portion defining a fluid chamber therein, a coupling element at a distal end of the body portion configured to couple the body portion to a catheter assembly such that the fluid chamber can be selectively placed in fluid communication with a lumen of the catheter assembly, and an actuator configured to expel a fluid from the fluid chamber and into a lumen of a catheter assembly to which the device is coupled.

The fluid can include sterile saline. The catheter assembly can include at least one of a catheter, a catheter hub, a catheter hub cap, a vascular catheter, a custom catheter, and an existing catheter. The device can allow for direct injection of the fluid into the catheter assembly at the time of attachment of the device to the catheter. The catheter flushing device can be pre-attached to the catheter assembly. The coupling element can be configured to couple to conventional catheters or catheter assemblies. The coupling element can include at least one of a Luer Lock® connector, a Clave® connector, and extension tubing. The device can include a circumferentially sealing dressing formed integrally with the coupling element. The coupling element can be or can include a hub cap, and the device can include a circumferentially sealing dressing configured to seal to the hub cap. The body portion can be used as a handle over which a circumferentially sealing dressing can be mounted and attached to the catheter assembly.

In another aspect, a method of placing and flushing a catheter is provided that includes inserting a catheter over an insertion needle into a patient, the catheter having a needle containment device coupled thereto, withdrawing the insertion needle from the catheter into the needle containment device, and transferring a volume of an injectable agent into an inner lumen of the catheter.

The method can include transferring the injectable agent into the inner lumen from a chamber within the needle containment device. The method can include sliding a sterile sealing dressing over the needle containment device and onto the catheter, wherein the needle containment device is sterile. The method can include adhering the dressing circumferentially around the catheter insertion site to create a sterile sealed chamber. The method can include detaching the needle containment device from the catheter or other component of a catheter assembly after adhering the dressing.

The method can include coupling a sterile flushing device having a fluid chamber defined therein to the catheter, actuating the flushing device to force the injectable agent from the fluid chamber into the inner lumen of the catheter, using the flushing device as a sterile handle, sliding a sterile dressing over the flushing device, circumferentially sealing the dressing around a catheter insertion site, and detaching the sterile flushing device from the catheter or other component of a catheter assembly.

The method can include coupling a sterile flushing device having a fluid chamber defined therein to the catheter, actuating the sterile flushing device to force the injectable agent from the fluid chamber into the inner lumen of the catheter, using the flushing device as a sterile handle to control and stabilize the catheter while unfurling and circumferentially adhering a dressing integrated therewith around a catheter insertion site, and detaching the flushing device from the catheter. The method can include adhering the dressing to a portion of the catheter or a catheter assembly.

BRIEF DESCRIPTION OF THE DRAWINGS

The invention will be more fully understood from the following detailed description taken in conjunction with the accompanying drawings, in which:

FIG. 1A is a side view of a system that includes a needle containment device coupled to a catheter assembly;

FIG. 1B is a side view of the system of FIG. 1A with a needle retracted into the needle containment device;

FIG. 1C is a side view of a needle assembly and related central channel structures shown in both a retracted and a deployed configuration;

FIG. 1D is a top view of the needle assembly and related central channel structures of FIG. 1C shown in both a retracted and a deployed configuration;

FIG. 1E is an exploded side view of the needle assembly and related central channel structures of FIG. 1C;

FIG. 1F is an exploded top view of the needle assembly and related central channel structures of FIG. 1C;

FIG. 1G is a top view of the system of FIG. 1A with a needle shown in a deployed configuration and a saline chamber shown in a full or pre-flush configuration;

FIG. 1H is a top view of the system of FIG. 1A with a needle shown in a retracted configuration and a saline chamber shown in an empty or post-flush configuration;

FIG. 1I is a top view of the needle containment device of FIG. 1A separated from the catheter assembly;

FIG. 2A is a side view of the system of FIG. 1A inserted into a patient;

FIG. 2B is a side view of the system of FIG. 2A with an insertion needle having been withdrawn into a saline flush needle containment device;

FIG. 2C is a side view of the system of FIG. 2A with saline flush having been injected from the needle containment device into the catheter;

FIG. 2D is a side view of the system of FIG. 2A with a dressing being mounted over the needle containment device;

FIG. 2E is a side view of the system of FIG. 2A with the dressing being adhered to the patient;

FIG. 2F is a side view of the system of FIG. 2A with the needle containment device being detached from the catheter-dressing complex;

FIG. 4A is a side view of the handle of FIG. 3A and an inserted catheter;

FIG. 4B is a side view of the handle of FIG. 4A coupled to the inserted catheter;

FIG. 4C is a side view of the handle of FIG. 4A after saline contained therein has been injected into the catheter and as a dressing is first being mounted over the handle;

FIG. 4D is a side view of the handle of FIG. 4A after the dressing has been slid down into position adjacent to a skin surface;

FIG. 4E is a side view of the handle of FIG. 4A after the dressing has been adhered to the skin surface;

FIG. 4F is a side view of the handle of FIG. 4A detached from the catheter-dressing complex;

FIG. 5A is a side view of the handle of FIG. 3D and an inserted catheter;

FIG. 5B is a side view of the handle of FIG. 5A coupled to the inserted catheter;

FIG. 5C is a side view of the handle of FIG. 5A after saline contained therein has been injected into the catheter and as a dressing is first being mounted over the handle;

FIG. 5D is a side view of the handle of FIG. 5A after the dressing has been slid down into position adjacent to a skin surface;

FIG. 5E is a side view of the handle of FIG. 5A after the dressing has been adhered to the skin surface;

FIG. 5F is a side view of the handle of FIG. 5A detached from the catheter-dressing complex;

FIG. 7A is an enlarged view of the system of FIGS. 1A-1I;

FIG. 7B is an enlarged view of the system of FIGS. 3A-3C;

FIG. 7C is an enlarged view of the system of FIGS. 3D-3F; and

FIG. 7D is an enlarged view of the system of FIGS. 6A-6F.

DETAILED DESCRIPTION

Figure 3A:
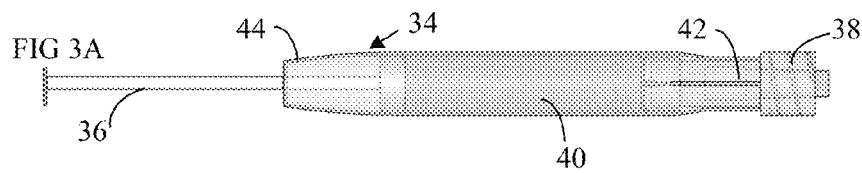
FIG. 3A is a side view of a saline flush handle configured to mate with a standard Luer Lock® type connection device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A person skilled in the art will appreciate that, while methods and devices are described herein in connection with catheters implantable in humans, the methods and devices can also be used in any instance in which a seal is desired around an elongate device implanted into or otherwise extending from a plant, an animal, and/or any non-living machine, structure, or system or in which a flushing capability is desired. In addition, while the methods and devices disclosed herein are described primarily with respect to intravenous catheters, they can also be used with any of a variety of other devices and other procedures including, without limitation, arterial monitoring lines, access sheaths for intravascular procedures such as angiography and stenting, access sheaths for intravascular therapeutic devices such as intra-aortic balloon pumps and ventricular support devices, etc.

Further details on catheter-dressing systems can be found in U.S. Publication No. 2012/0197204, filed on Jan. 13, 2012 and entitled "SNAP-SEAL STERILE INTRAVASCULAR CATHETER-DRESSING SYSTEM," the entire contents of which are incorporated herein by reference. Further details on catheter-dressing systems can also be found in U.S. Publication No. 2011/0106014, filed on Oct. 28, 2010 and entitled "SEALED STERILE CATHETER DRESSINGS," the entire contents of which are incorporated herein by reference.

FIG. 1A shows a side view of a catheter flushing or injection system 10 that includes a needle containment device 12. The needle containment device 12 can be attached to a catheter assembly 14. The system 10 can also include a dressing, as described in further detail below. The needle containment device 12 can contain a volume of injectable agent. While saline is generally referred to herein, it will be appreciated that the injectable agent can be or can include any of a variety of fluids, solutions, etc., including without limitation therapeutic agents, blood, blood substitutes, nourishing agents, flush solutions, and so forth. In addition, as used herein, the terms "sterile saline" and "saline" refer not only to pure saline, but also to solutions that include saline and one or more other components, such as anticoagulants (e.g., Heparin). In the illustrated embodiment, a full sterile saline bag 16 is contained in the "top" half of a chamber internal to the needle containment device 20. A roller pin 18 attached to an upper sliding collar 20 can be configured to compress the bag 16 as the upper sliding collar 20 is advanced distally, thereby flushing the contained saline into the catheter assembly 14. The system 10 can also include an insertion needle 22 that can be attached to a lower sliding collar 24 of the needle containment device 12. In FIG. 1A, the needle 22 (and the attached collar 24) are shown in a deployed position in which the needle 22 is inserted through the catheter assembly 14 with a tip of the needle extending beyond the distal catheter end (e.g., for insertion purposes). A saline injection hole/channel 26 can be closed when the needle 22 is in this deployed position (as will be seen, when the needle 22 is withdrawn into the needle containment device 12, the hole/channel 26 can be exposed, which then allows injection of the contained saline into the catheter assembly 14, e.g., for the purpose of flushing the catheter assembly of blood).

It should be noted that other saline containment and injection actuators can be used, including a vertically collapsible "accordion" actuator or a central plunger actuator (as described below and shown in FIGS. 6A-6F). In an "accordion" type compression actuator, the saline or other injectable agent can be contained in a soft expanded accordion container, and compression of this expanded accordion chamber (filled with saline in its expanded form) can compress the chamber and empty the saline. This accordion chamber can be contained inside the needle containment device 12 with a compression actuator connected to the upper sliding collar 20, or one side of the needle containment device 12 can be occupied by this mounted but exposed accordion chamber. Preferably, the maximum outer diameter of the saline-containing needle containment device 12 is less than or equal to the diameter of the catheter hub mounting point 28. This can allow a dressing to be slid over the needle containment device 12 so that it can be mounted at the specified catheter hub mating point 28. In some embodiments, the dressing can form a circumferential seal around a specific mating point on the catheter hub. In other embodiments, the dressing can form a circumferential seal around other portions of a catheter assembly, such as a catheter hub cap or the implanted catheter itself.

FIG. 1B is a side view that shows the needle 22 retracted into the needle containment device 12 (via the lower sliding collar 24), and the saline flush injected into the catheter (via compression of the contained saline bag by the upper collar 20 and its attached "rolling pin" 18).

FIG. 1C is a side view of the needle assembly and related central channel structures which can allow for opening of a saline injection hole/channel when the needle is withdrawn. As shown in the top part of FIG. 1C, the hole/channel 26 can be open when the needle 22 is in the retracted position. As shown in the bottom part of FIG. 1C, the hole/channel 26 can be closed (e.g., obstructed by the needle 22 or a structure coupled thereto) when the needle 22 is in the deployed position. FIG. 1D is a top view of the needle assembly and related central channel structures which can allow for opening of a saline injection hole/channel when the needle 22 is withdrawn.

FIG. 1E is an exploded side view of the needle assembly and related central channel components. The needle 22 can include a T-shaped proximal end which can be operably attached to the lower collar 24 shown in FIGS. 1A and 1B, such that sliding of the collar 24 along the exterior of the needle containment device 12 effects corresponding longitudinal translation of the needle 12. A hole-containing component 30 can be attached to or formed integrally with the needle containment device 12 body. The inner channel of the catheter assembly 14 is shown on the right. FIG. 1F is an exploded top view of the needle assembly and related central channel components.

FIG. 1G is a top view of the needle containment device 12 with the needle 22 deployed and the saline chamber 16 still full. FIG. 1H is a top view of the needle containment device 12 with the needle 22 retracted, after injection/flushing of the saline into the catheter assembly 14. FIG. 1I shows the needle containment device 12 detached from the inserted and flushed catheter, for example after the needle containment device has been used as a handle for mounting of a circumferential sealing dressing (e.g., a dressing as disclosed in the references incorporated above).

In one embodiment, some or all of the following steps can be executed in connection with the system 10 illustrated in FIGS. 1A-1I. First, the catheter body of the catheter assembly 14 can be inserted into a patient. Second, the insertion needle 22 can be withdrawn from the catheter and into the needle containment device 12 by sliding the lower collar 24 proximally. Third, saline flush can be injected from the needle containment device 12 into the inserted catheter by sliding the upper collar 20 distally. Fourth, a sterile circumferentially-sealing dressing 30 can be slid/mounted over the needle containment device 12 and into final sealing/securing position over the inserted catheter. Fifth, an adhesive backing 32 can be removed from the dressing and the dressing can be circumferentially sealed around the catheter insertion site. Sixth, the needle containment device can be disconnected/removed from the catheter-dressing complex.

FIG. 2A is a side view of the system 10 of FIGS. 1A-1I after insertion of the catheter into a blood vessel. FIG. 2B is a side view that shows the insertion needle 22 having been withdrawn into the saline flush needle containment device 12. This can be achieved by sliding the lower hemi-cylindrical collar 24 back (i.e., proximally away from the distal skin insertion site). The collar 24 and/or the needle 22 can be configured to lock into place when withdrawn to a fully retracted position or any of a variety of positions intermediate to the fully retracted position and the fully deployed position.

FIG. 2C is a side view that shows the saline flush contained in the flush compartment of the needle containment device 12 having been injected into the catheter 14. This can be achieved by sliding the upper hemi-cylindrical collar 20 forward (i.e., distally towards the distal skin insertion site), thereby compressing the saline container 16 and forcing the saline through the opening 26 in the central shaft, which opening 26 can be exposed by withdrawal of the needle 22. FIG. 2D shows an exemplary integrated mating dressing 30 being mounted over the sterile handle provided by the needle containment device 12. FIG. 2E shows the dressing 30 slid into position and mated with specific mating features of the catheter hub. An adhesive backing portion 32 of the dressing 30 can be peeled away at this time to adhere the dressing to the skin surface and thereby form a circumferential seal around the catheter and the catheter insertion site. The mating interaction between the dressing and catheter can also serve to fully secure the catheter to the patient, preventing both longitudinal and rotational movement.

FIG. 2F shows the needle containment device 12 detached from the catheter-dressing complex. The needle containment device 12, which now safely contains the insertion needle 22 and is devoid of saline, can now be ready for safe disposal.

FIG. 3A is a side view of a saline flush handle 34 configured to mate with a standard Luer Lock® type connection device. The handle 34 is shown as it might look after removal from its sterile packaging. A plunger 36 is shown in a withdrawn position, ready to inject once a Luer Lock® connector 38 is connected to a catheter hub after successful catheter insertion. Sterile saline or other injectable agents can be contained in a chamber 40 in the handle 34. Slits 42 in a portion of the handle "skirt" that fits over the Luer Lock® connector 38 can enable the skirt to shrink in diameter as a dressing 30 is slid over the handle 34 to mount onto the neck of the Luer Lock® connector 38 (as depicted in FIG. 4D, below). Preferably, the maximum outer diameter of the saline flush handle 34 is less than or equal to the diameter of the specified hub cap mounting point. This can allow the dressing 30 to be slid over the handle 34 so that it can be mounted at the specified catheter hub cap mating point. The proximal "plunger handle" end 44 of the saline flush handle 34 can be uniquely tapered to allow easy mounting of the dressing 30 onto the handle 34. In particular, the proximal end 44 of the handle 34 can have a first diameter that gradually tapers distally into a second diameter that is greater than the first diameter. As noted above, the first and second diameters, and the maximum outer diameter of the handle 34, can all preferably be less than or equal to the outer diameter of a dressing mating point on the catheter, catheter hub, or catheter hub cap.

Figure 3B:
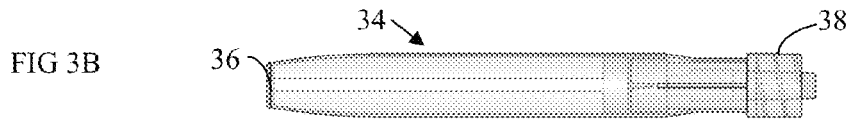
FIG. 3B is a side view of the handle of FIG. 3A in an injected position.
Figure 3C:
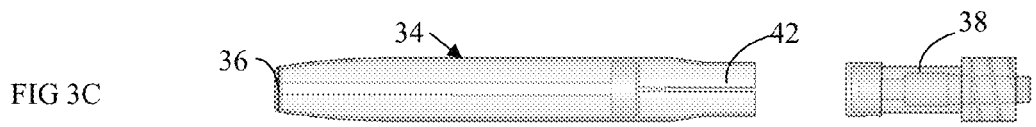
FIG. 3C is a side view of the handle of FIG. 3A disconnected from the Luer Lock® connector.

FIG. 3B is a side view of the saline flush handle 34 with the plunger 36 in the injected position (after injecting the sterile saline or other injectable agent into the Luer Lock® connector 38 and catheter, for example to flush through blood that would otherwise cause clotting and clogging of the newly inserted catheter). FIG. 3C is a side view of the saline flush handle disconnected from the Luer Lock® connector 38. Disconnection of the handle can be performed, for example, after a sterile dressing 30 has been mounted to the Luer Lock®-catheter complex as shown in FIG. 4F.

Figure 3D:
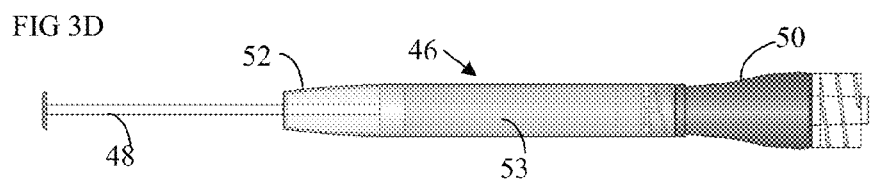
FIG. 3D is a side view of a saline flush handle configured to mate with a Clave® needleless connection device.

FIG. 3D is a side view of a saline flush handle 46 configured to mate with a Clave® needleless connection device. The handle 46 is shown as it might look after removal from its sterile packaging. The plunger 48 is shown in a withdrawn position, ready to inject once a Clave® connector 50 is connected to a catheter hub after successful catheter insertion. Sterile saline or other injectable agents can be contained in a chamber 53 in the handle. Like the embodiment shown in FIG. 3A, the saline flush handle 46 of FIG. 3D can include a uniquely tapered proximal end 52 to allow easy mounting of the dressing 30 onto the handle 46. In particular, the proximal end 52 of the handle 46 can have a first diameter that gradually tapers distally into a second diameter that is greater than the first diameter. The first and second diameters, and the maximum outer diameter of the handle 46, can all preferably be less than or equal to the outer diameter of a dressing mating point on the catheter, catheter hub, or catheter hub cap.

Figure 3E:
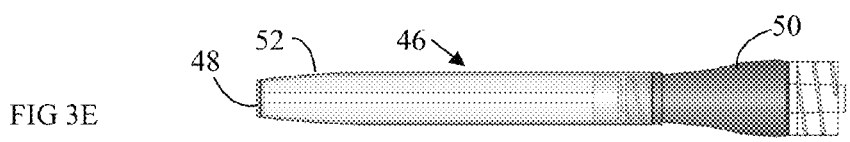
FIG. 3E is a side view of the handle of FIG. 3D in an injected position.
Figure 3F:
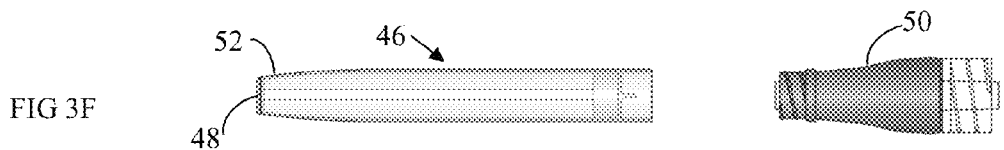
FIG. 3F is a side view of the handle of FIG. 3D disconnected from the Clave® connector.

FIG. 3E is a side view of the saline flush handle 46 with the plunger 48 in the injected position (after injecting the sterile saline or other injectable agent into the Clave® connector 50 and catheter, for example to flush through blood that would otherwise cause clotting and clogging of the newly inserted catheter). FIG. 3F is a side view of the saline flush handle disconnected from the Clave® connector 50. Disconnection of the handle can be performed, for example, after the sterile dressing has been mounted to the Clave®-catheter complex as shown in FIG. 5F.

While saline flush handles are disclosed that are specifically configured to couple using Luer Lock® or Clave® type connectors, it will be appreciated that the saline flush handles can be readily adapted to other standard or non-standard connectors.

In one embodiment, some or all of the following steps can be executed in connection with the system illustrated in FIGS. 3A-3C. First, the saline flush handle 34 and Luer Lock® connector 38 complex can be mounted to an inserted catheter assembly 14. Second, the catheter can be flushed with sterile saline. Third, a circumferentially-sealing sterile dressing 30 can be placed over the handle and the inserted catheter. Fourth, the saline flush handle can be removed from the inserted catheter.

FIG. 4A is a side view of the sterile saline flush handle 34 and attached Luer Lock® connector 38, which can be connected to an inserted "standard vascular" catheter 14 or any of a variety of other catheters having a corresponding Luer Lock® connector. FIG. 4B is a side view showing the sterile saline flush handle 34 attached to the catheter 14. FIG. 4C is a side view of the sterile saline flush handle 34 after the saline has been injected into the catheter, and as a circumferential sealing dressing 30 is first being mounted over the handle. The tapered proximal tip 36 of the handle can facilitate sliding of the dressing 30 onto the handle 34.

FIG. 4D is a side view of the sterile saline flush handle 34 and Luer Lock®-catheter complex after the dressing 30 has been slid down into final mounting sealing position, but before the adhesive backing 32 has been peeled away (for final adhesion of the dressing to the skin). It will be appreciated that the dressing can be configured to form a seal at a particular mating site on the Luer Lock® catheter hub cap. The dressing can also be configured to form a seal with other components of the catheter assembly, such as a catheter hub or the implanted catheter itself. FIG. 4E is a side view of the sterile saline flush handle 34 and Luer Lock®-catheter complex after the dressing 30 has been adhered to the skin in final mounting securing position. FIG. 4F is a side view showing detachment of the sterile saline flush handle 34 from the mounted and secured Luer Lock®-catheter-dressing complex. Any of a variety of structures or techniques can be used to detachably couple the handle 34 to the Luer Lock® hub cap, such as a threaded interface, a friction fit, a frangible portion, and so forth.

In one embodiment, some or all of the following steps can be executed in connection with the system illustrated in FIGS. 3D-3F. First, the saline flush handle 46 and Clave® connector 50 complex can be mounted to an inserted catheter assembly 14. Second, the catheter can be flushed with sterile saline. Third, a circumferentially-sealing sterile dressing 30 can be placed over the handle and the inserted catheter. Fourth, the saline flush handle 46 can be removed from the inserted catheter.

FIG. 5A is a side view of the sterile saline flush handle 46 and attached Clave® connector 50, which can be connected to an inserted "standard vascular" catheter 14 or any of a variety of other catheters having a corresponding Clave® connector. FIG. 5B is a side view showing the sterile saline flush handle 46 and Clave® connector 50 attached to the catheter 14. FIG. 5C is a side view of the sterile saline flush handle 46 after the saline has been injected into the catheter, and as a circumferential sealing dressing 30 is first being mounted over the handle. The tapered proximal tip 52 of the handle can facilitate sliding of the dressing 30 onto the handle 46.

FIG. 5D is a side view of the sterile saline flush handle 46 and Clave®-catheter complex after the dressing 30 has been slid down into final mounting sealing position, but before the adhesive backing 32 has been peeled away (for final adhesion of the dressing to the skin). It will be appreciated that the dressing can be configured to form a seal at a particular mating site on the Clave® catheter hub cap. The dressing can also be configured to form a seal with other components of the catheter assembly, such as a catheter hub or the implanted catheter itself. FIG. 5E is a side view of the sterile saline flush handle 46 and Clave®-catheter complex after the dressing 30 has been adhered to the skin in final mounting securing position. FIG. 5F is a side view showing detachment of the sterile saline flush handle 46 from the mounted and secured Clave®-catheter-dressing complex. Any of a variety of structures or techniques can be used to detachably couple the handle 46 to the Clave® hub cap, such as a threaded interface, a friction fit, a frangible portion, and so forth.

Figure 6A:
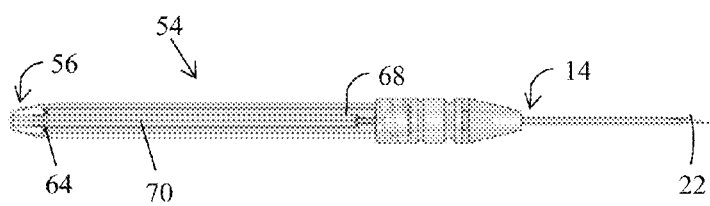
FIG. 6A is a side view of a system that includes a needle containment device.

FIG. 6A shows a side view of another embodiment of a catheter flushing or injection system that includes a needle containment device 54. The needle containment device 54 can include a central plunger actuator assembly 56 and can be attached to a catheter 14. The system can also include a dressing, as described above. The system is shown as it would appear just after its removal from its sterile packaging and in an insertion-ready state. The plunger assembly 56 can include a handle portion 66 and two or more elongate feet 62 which can be configured to spread apart from one another. The plunger assembly 56 can be disposed within a central channel 68 formed in the needle containment device 54. The needle containment device 54 can also include a fluid chamber 70 disposed around the central channel 68 that can contain any of a variety of injectable agents, such as sterile saline. A plunger ring 64 can be slidably disposed about the central channel 68, and can define the proximal wall of the fluid chamber 70 such that the fluid chamber 70 has a variable volume based on the position of the plunger ring 64. The needle containment device 54 and/or the plunger handle 66 can include a uniquely tapered proximal end to allow easy mounting of a dressing 30 onto the needle containment device 54. In particular, the proximal end 76 of the needle containment device 54 and the plunger handle 66 can each have a first diameter that gradually tapers distally into a second diameter that is greater than the first diameter. The first and second diameters of each component, and the maximum outer diameter of the needle containment device 54, can all preferably be less than or equal to the outer diameter of a dressing mating point on the catheter, catheter hub, or catheter hub cap.

Figure 6B:
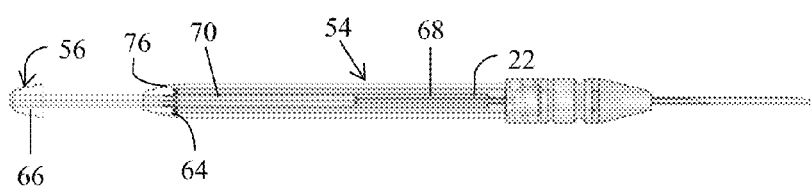
FIG. 6B is a side view of the system of FIG. 6A with a plunger assembly partially withdrawn proximally to retract an insertion needle coupled thereto into the needle containment device.

FIG. 6B shows the system of FIG. 6A with the plunger assembly 56 partially withdrawn proximally to retract an insertion needle 22 coupled thereto into the needle containment device 54. The distal ends of the elongate feet 62 can be attached to the needle 22 using any of a variety of techniques, such as a friction fit, interference fit, snap fit, etc.

Figure 6C:
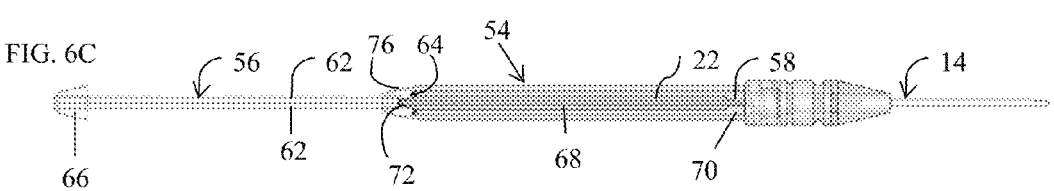
FIG. 6C is a side view of the system of FIG. 6A with the plunger assembly fully withdrawn proximally such that the insertion needle is fully contained within the needle containment device.

FIG. 6C shows the system of FIG. 6A with the plunger assembly 56 fully withdrawn proximally such that the insertion needle 22 is fully contained within the needle containment device 54. The system can be configured to lock the needle in a retracted position for safe disposal. For example, when the needle 22 is fully retracted, one or more spring detents 72 formed on a head 60 of the needle 22 can expand radially outwards to engage a proximal locking surface 74, thereby preventing subsequent proximal movement of the needle 22. Alternatively, or in addition, radial retraction of the inner channel wall after the insertion needle head has been withdrawn past it can serve to lock the needle into the withdrawn position.

As also shown in FIG. 6C, a hole 58 can be provided in the sidewall of the central channel 68 of the needle containment device 54. The hole 58 can be exposed by full withdrawal of the needle 22, and can provide an aperture through which saline or other injectable agents stored in the fluid chamber 70 can be transferred into the central channel 68 and the attached catheter assembly 14.

Figure 6D:
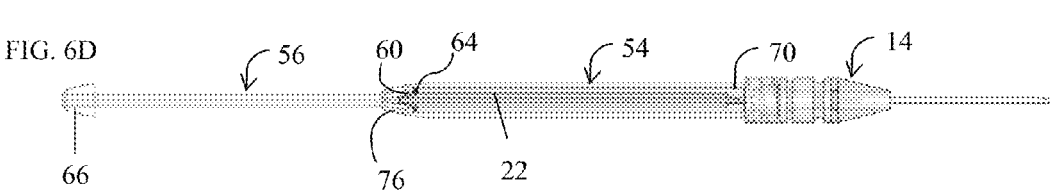
FIG. 6D is a side view of the system of FIG. 6A with the plunger assembly disengaged from the head of the needle and with feet of the plunger assembly just beginning to split around the locked needle head.

FIG. 6D shows the system with the plunger assembly 56 disengaged from the head 60 of the needle 22. In particular, the feet 62 of the plunger assembly 56 can be configured to disengage from the head 60 of the needle 22 when a distal force is applied to the plunger assembly 56 while the needle 22 is locked in the retracted position. FIG. 6D shows the feet 62 of the plunger assembly 56 just beginning to split around the locked needle head 60, so that the spread feet 62 begin to push down onto the plunger ring 64 in the sterile saline chamber. The proximal end of the needle head 60 locking point (e.g., the spring detents 72) can have a conical shape to allow this splitting of the plunger feet 62 to naturally occur as the plunger assembly 56 is pushed distally.

Figure 6E:
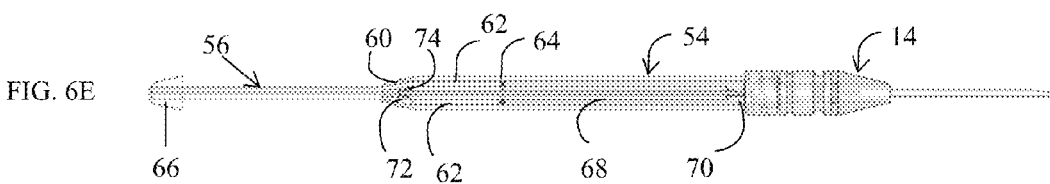
FIG. 6E is a side view of the system of FIG. 6A with the plunger assembly and a plunger ring advanced into the needle containment device.
Figure 6F:
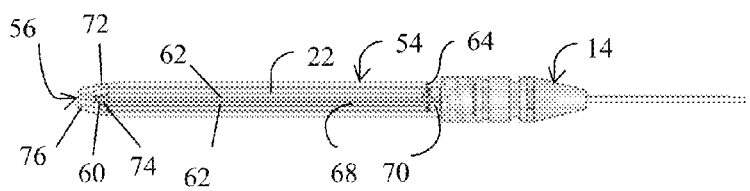
FIG. 6F is a side view of the system of FIG. 6A with the plunger assembly fully advanced into the needle containment device.

FIG. 6E shows the system with the plunger assembly 56 and plunger ring 64 further advanced into the needle containment device 54 (roughly ⅓ of the saline having been injected into the catheter 14 through the hole 58 in the central channel exposed by the withdrawal of the needle 22). FIG. 6F shows the assembly with the saline flush fully injected. At this time, any of the methods described above can be used to mount a sterile sealing dressing 30 over the needle containment device 54 and into a final mating position on the catheter assembly 14, and to detach the needle containment device 54 from the catheter hub or hub cap.

FIG. 7A shows an enlarged view of the system of FIGS. 1A-1I. FIG. 7B shows an enlarged view of the system of FIGS. 3A-3C. FIG. 7C shows an enlarged view of the system of FIGS. 3D-3F. FIG. 7D shows an enlarged view of the system of FIGS. 6A-6F.

Any of the components of the devices disclosed herein can be transparent or semi-transparent to allow visualization of blood, saline, or other materials contained therein. Any of the needle containment devices disclosed herein can include a lockout feature to lock the needle in the retracted position to facilitate safe removal and disposed. The interior or exterior of any of the components of the devices disclosed herein can be coated and/or impregnated with a sterilizing agent.

The systems described herein can also be packaged in the form of a kit including dressings, catheters, hubs, hub caps, hub protection devices, insertion needles, needle containment devices, and/or other components of various sizes and shapes for use with various sized catheters, patients, body parts, etc. The kit can also include various items for sterile site preparation and sterile catheter insertion, such as tourniquets, preparation solutions, solution applicators, sterile saline flush, and/or sterile gloves. The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a caregiver immediately prior to a catheterization procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before use. First, a new or used device is obtained and if necessary cleaned. The device can then be sterilized. In one sterilization technique, the instrument is placed in a closed and sealed container, such as a plastic or TYVEK bag. The container and device are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical field.

It is preferred that the device is sterilized. This can be done by any number of ways known to those skilled in the art including beta or gamma radiation, ethylene oxide, steam, and/or a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A catheter system comprising:
   a catheter assembly comprising an implantable catheter and catheter hub formed at a proximal end of the implantable catheter;
   an insertion needle adapted for disposition within an inner lumen of the implantable catheter with a tip extendable distally therefrom to facilitate inserting a catheter over the needle into a patient, and
   a needle containment device configured to be coupled to, and releasable detachable from, the catheter assembly, such that when coupled, the needle containment device extends proximally from the catheter assembly and is coupleable to the insertion needle disposed through the lumen of the implantable catheter to remove the needle from the implantable catheter and lock it in a retracted position within the containment device;
   wherein the needle containment device further comprises a chamber filled with an injectable agent, the needle containment device being configured to selectively place the chamber in fluid communication with the inner lumen of the implantable catheter; and
   an actuator adapted to expel the injectable agent from the chamber of the needle containment device into the inner lumen of the implantable catheter after needle retraction and prior to detachment of the needle containment device from the catheter assembly.

2. The system of claim 1, further comprising a dressing assembly configured to slide over the needle containment device and catheter hub to form a circumferential seal around the catheter hub and a catheter insertion site.

3. The system of claim 1, wherein the injectable agent comprises sterile saline or other solution suitable for flushing a catheter.

4. The system of claim 1, wherein the chamber comprises a flexible bag.

5. The system of claim 1, wherein the needle containment device includes a first hemi-cylindrical collar disposed about an exterior surface of a body portion of the needle containment device, the collar being coupled to a roller configured to compress the chamber.

6. The system of claim 5, wherein sliding the first collar distally relative to the body portion causes the roller to compress the chamber and force the injectable agent into the inner lumen of the implantable catheter.

7. The system of claim 1, wherein the needle containment device includes a second hemi-cylindrical collar disposed about an external surface of a body portion of the needle containment device, the collar being coupled to the insertion needle.

8. The system of claim 7, wherein sliding the second collar proximally relative to the body portion is effective to withdraw the insertion needle from the implantable catheter and into the needle containment device.

9. The system of claim 1, wherein the needle containment device includes an aperture that controls fluid communication between the chamber and the inner lumen of the implantable catheter.

10. The system of claim 9, wherein the insertion needle blocks the aperture when the insertion needle is in a deployed configuration.

11. The system of claim 10, wherein the aperture is open when the insertion needle is in a retracted configuration.

12. The system of claim 1, wherein the needle containment device has a maximum outer diameter that is less than or equal to a diameter of a mating point on the catheter assembly to which a dressing can be mated.

13. The system of claim 1, wherein a circumferentially-sealing catheter dressing is adapted to be slid over the needle containment device.

14. The system of claim 1, wherein the needle containment device is divided into two or more separate compartments, at least one compartment being filled with the injectable agent.

15. The system of claim 1, wherein the needle containment device includes a sliding collar whose movement distally towards the catheter assembly effects pressure based transfer of the injectable agent from the chamber into the catheter assembly.

16. The system of claim 1, wherein the needle containment device includes a central plunger, proximal withdrawal of the plunger out of the needle containment device serves to remove the insertion needle from the implantable catheter and lock it into a retracted position, and subsequent distal movement of the plunger serves to effect transfer of the injectable agent from the chamber to the catheter assembly.

17. A method of placing and flushing a catheter using the catheter system of claim 1, comprising:
   inserting a catheter over an insertion needle into a patient, the catheter having a needle containment device coupled thereto;
   withdrawing the insertion needle from the catheter into the needle containment device; and
   transferring a volume of an injectable agent into an inner lumen of the catheter.

18. The method of claim 17, wherein the method further comprises transferring the injectable agent into the inner lumen from a chamber within the needle containment device.

19. The method of claim 17, further comprising sliding a sterile sealing dressing over the needle containment device and onto the catheter, wherein the needle containment device is sterile.

20. The method of claim 19, further comprising adhering the dressing circumferentially around the catheter insertion site to create a sterile sealed chamber.

21. The method of claim 20, further comprising detaching the needle containment device from the catheter or other component of a catheter assembly after adhering the dressing.

22. The method of claim 17, further comprising:
   coupling a sterile flushing device having a fluid chamber defined therein to the catheter;
   actuating the flushing device to force the injectable agent from the fluid chamber into the inner lumen of the catheter;
   using the flushing device as a sterile handle, sliding a sterile dressing over the flushing device;
   circumferentially sealing the dressing around a catheter insertion site; and
   detaching the sterile flushing device from the catheter or other component of a catheter assembly.

23. The method of claim 17, further comprising:
   coupling a sterile flushing device having a fluid chamber defined therein to the catheter;
   actuating the sterile flushing device to force the injectable agent from the fluid chamber into the inner lumen of the catheter;
   using the flushing device as a sterile handle to control and stabilize the catheter while unfurling and circumferentially adhering a dressing integrated therewith around a catheter insertion site; and
   detaching the flushing device from the catheter.

24. The method of claim 23, further comprising adhering the dressing to a portion of the catheter or a catheter assembly.

* * * * *